United States Patent [19]
Gumb et al.

[11] Patent Number: 5,997,471
[45] Date of Patent: Dec. 7, 1999

[54] APPARATUS FOR GUIDING SURGICAL INSTRUMENTS FOR ENDOSCOPIC SURGERY

[75] Inventors: Lothar Gumb, Karlsdorf-Neuthard; Aribert Schäf, Bruchsal; Rainer Trapp, Graben-Neudorf; Gerhard Buess; Marc Schurr, both of Tübingen, all of Germany

[73] Assignee: Forschungszentrum Karlsruhe GmbH, Karlsruhe, Germany

[21] Appl. No.: 08/917,522

[22] Filed: Aug. 26, 1997

Related U.S. Application Data

[63] Continuation of application No. PCT/EP96/00990, Mar. 8, 1996.

[30] Foreign Application Priority Data

Mar. 10, 1995 [DE] Germany ............................ 195 08 365

[51] Int. Cl.[6] ........................................................ A61B 1/04
[52] U.S. Cl. ............................ 600/102; 600/114; 606/130
[58] Field of Search .................................. 600/101, 102, 600/114; 606/130; 604/95

[56] References Cited

U.S. PATENT DOCUMENTS

| | | | |
|---|---|---|---|
| 4,638,798 | 1/1987 | Shelden et al. | 606/130 |
| 5,154,723 | 10/1992 | Kubota et al. | 600/102 |
| 5,695,500 | 12/1997 | Taylor et al. | 606/130 |

FOREIGN PATENT DOCUMENTS

| | | |
|---|---|---|
| 94 16 957 | 2/1995 | Germany . |
| 196 09 034 | 9/1996 | Germany . |
| WO 94/21188 | 9/1994 | WIPO . |

*Primary Examiner*—John P. Leubecker
*Attorney, Agent, or Firm*—Klaus J. Bach

[57] ABSTRACT

In an apparatus for guiding surgical instruments during endoscopic surgery including a carrier on which a support member is rotatably mounted about a first axis and a housing structure is mounted on the support member so as to pivot about a second axis which is spaced from the housing structure and intersects the first axis in an invariant point and the housing slidably supports an instrument shaft having an axis also extending through the invariant point and an end which is mounted on a guide member, which is axially movably supported on a guide housing extending from the housing structure parallel to the instrument shaft, a camera is firmly supported on the guide housing in alignment with the instrument shaft so as to be axially movable but not rotatable with the instrument shaft whereby an image transmitted from a lens system at the front end of the instrument shaft to the camera at the rear end of the shaft is shown at a given top-to-bottom orientation independently the rotational position of the instrument shaft.

3 Claims, 3 Drawing Sheets

APPARATUS FOR GUIDING SURGICAL INSTRUMENTS FOR ENDOSCOPIC SURGERY

This application is a continuation of PCT/EP96/00990 filed Mar. 3, 1996.

BACKGROUND OF THE INVENTION

The invention resides in an apparatus for guiding surgical instruments for endoscopic surgery while the instruments are mounted as a shank which is supported so as to be pivotable about a so-called invariant point.

During laparoscopic surgery, the surgeon operates on the basis of a monitor picture. An endoscope with a camera and the instruments required for the operation are inserted into the body of a patient, for example, by a trocar. The endoscope and the instruments are so supported that they can be moved only about the so-called invariant point which is within the body of the patient and which represents the trocar insertion point. In this way, the endoscopic system and the instruments each can be controlled with the same positioning system. However, the camera should be oriented, for example, by the CCD chip of a camera, in a direction toward the floor, that is, the support point of the surgeon, independently of the movement of the instruments. If the monitor picture would be turned, the spatial orientation of the surgeon during endoscopic surgery may be detrimentally affected.

WO 94/21188 discloses such a mechanical guide system for endoscopic surgery wherein the instrument is inserted into a body for a surgical procedure or for observation through the sleeve of a trocar and the instrument effecter, which is mounted at the end of a shaft, is movable within the body cavity in all degrees of freedom; the invariant point however is maintained. In the system described a camera is mounted as an effecter on the free end of the laparoscope and is movable linearly with the laparoscope shaft.

Endoscopes usually have a prism arranged at their front end which is usually inclined by 30° whereby rotation of the endoscope permits observing an area within the body. Upon rotation of the effecter for observing the surrounding area within the body, a camera rigidly supported on the endoscopic as shown in WO 94/21188 provides, with the respect to the position of the surgeon, that is, the floor, a proper picture orientation only for the horizontal and center position of the camera. In all other positions of the CCD chip in the camera, the spatial orientation is changed, that is, the camera and the endoscope must be especially controlled so as to prevent rotation of the monitor picture. This requires a substantial technical effort. The rotation of the endoscope consequently detrimentally affects the orientation for the surgeon, for example, in the abdominal cavity, since the "top" and "bottom" of the camera picture may be different from the actual top and bottom with respect to the position of the surgeon.

Another guide system for a surgical observation apparatus is disclosed in DE-GM 94 16 957. The system described therein is principally similar to the above described system so that the same comments apply.

It is therefore the object of the present invention to provide an apparatus for guiding surgical instruments particularly for use in endoscopic surgery wherein, during rotation of the endoscope for the spatial observation in a body cavity, the picture transmitted to the camera and consequently, to the monitor screen is always properly oriented so that the "top" and "bottom" are properly presented.

SUMMARY OF THE INVENTION

In an apparatus for guiding surgical instruments during endoscopic surgery including a carrier on which a support member rotatably mounted about a first axis and a housing structure mounted on the support member so as to pivot about a second axis which is spaced from the housing structure and intersects the first axis in an invariant point and the housing slidably supports an instrument shaft with an axis also extending through the invariant point and with an end which is mounted on a guide member, that is, axially movably supported on a guide housing extending from the housing structure parallel to the instrument shaft, a camera is firmly supported on the guide housing in alignment with the instrument shaft so as to be axially movable but not rotatable therewith whereby a picture transmitted from a lens system at the front end of the instrument shaft to the camera at the rear end of the shaft is shown at a given top-to-bottom orientation independently of the rotational position of the instrument shaft.

Further, the guide member includes a front part which is slidably supported on the guide housing as well as on a plate which is mounted on the side thereof and to which another support plate is attached. The other support plate receives a gear meshing with another intermediate gear driven thereby. The support plate carries, on the side opposite the gear arrangement, a motor for driving the gears, the camera being mounted onto the motor.

In a guide structure which is arranged at the side and which is attached to the support plate for supporting the upper end of the instrument shaft, there is a rotatable adapter which can be rotated by a gear, which is disposed thereon and which meshes with the intermediate gear. The adapter receives the instrument shaft and is adapted to rotate it and, together therewith, the effecter.

Also, in accordance with the invention the end of the shaft adjacent the effecter is supported for example in a trocar so as to be movable therein and removable therefrom. The shaft is engaged alone or together with the trocar in the receiving opening of a trocar mount attached to the angle member and engaged by a locking lever so that it is loosely held and is removable when the locking lever is pivoted out of the way.

With the kinematics generated by the arrangement of the various axes, the instrument, that is, the effecter is rotated cone-like, like a rigid body around the invariant point. The camera mounted on the instrument shaft no longer changes the top to bottom orientation when the shaft is rotated as it remains in a properly oriented position. Consequently, from a view point of the surgeon, top and bottom of the monitor picture remain unchanged.

Details of the present invention will be described below on the basis of the accompanying drawings.

DESCRIPTION OF A PREFERRED EMBODIMENT

The main application for the apparatus is the observation of the operation area during minimal invasive endoscopic surgery. In such applications, an optical system is utilized which includes at the front end as an effecter 15 a prism which is arranged for example, at an angle of 30°. The prism is disposed at the end of a tube, that is, in this case, an instrument shaft 10 and transmits a picture, which is illuminated by light transmitted via a glass fiber cable, to a picture receiving element, for example, a CCD chip of an electronic camera 16. The beam path in the shaft 10 is similar to that of a telescope wherein the CCD chip is disposed in the image plane of the system. In such an arrangement, however, the problems regarding picture orientation described earlier will normally occur. With the apparatus according to the invention, the camera 16 and the CCD chip are therefore not turned when the effecter 13 is rotated.

Figure 3:
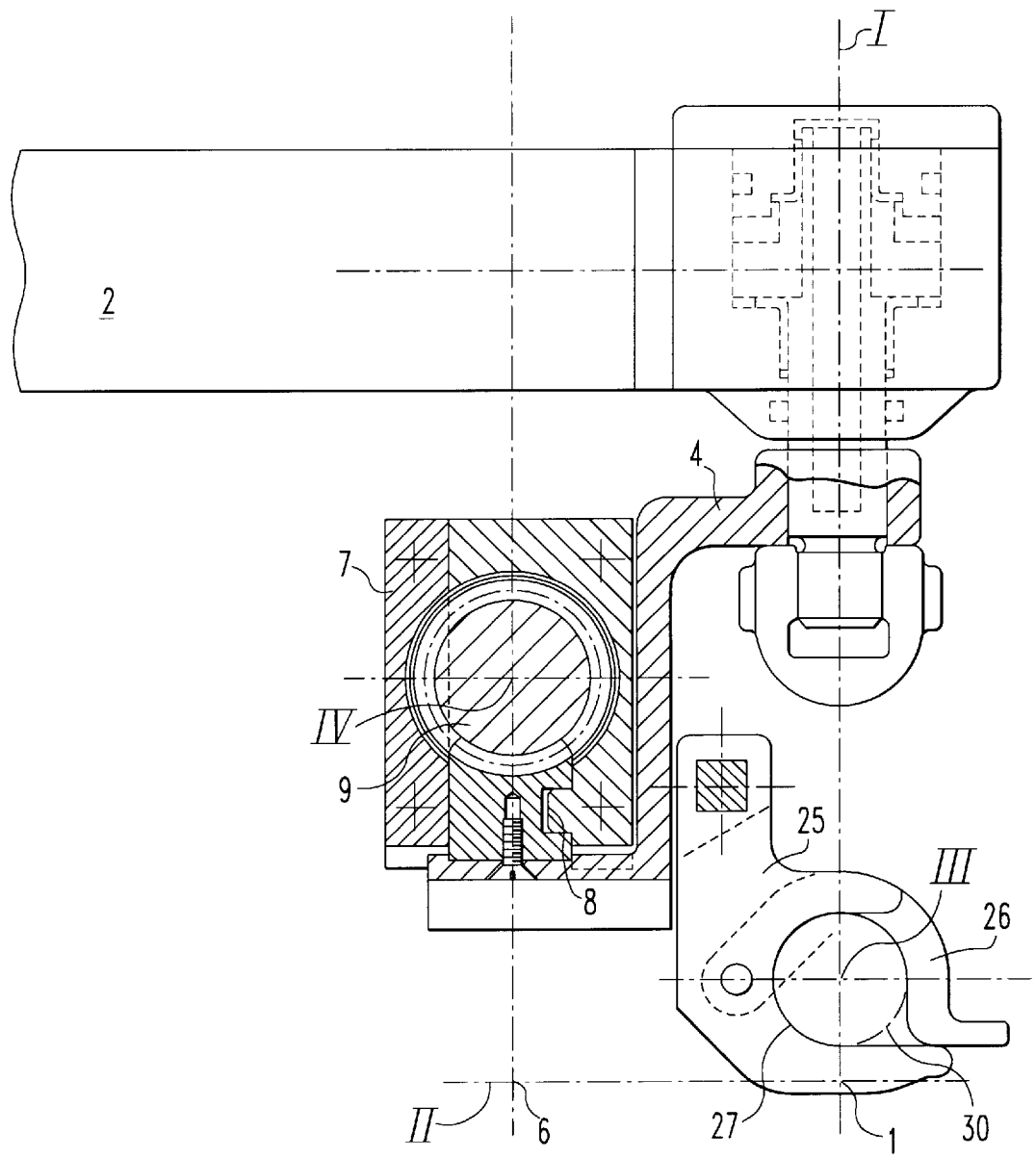
FIG. 3 is a cross-sectional view taken along line 1—1 of FIG. 1.

The apparatus according to the invention has four axes I, II, III an IV wherein axes I,II and III are axes of rotation and an axis IV is a linear slide axis. The main axis is axis I which is, as shown in FIG. 3, stationary with respect to a carrier 2 and which extends vertically and through the invariant point 1. However, it could be arranged, in principle, oriented in any other way. The whole arrangement with all the components can be rotated about the axis I by a motor or manually by 360°. The axis II is a pivot axis which is subordinate to the axis I and extends normal to the axis I. It intersects the axis I and is rotated with it, or, respectively, around it. The axis III forms the longitudinal axis of the instrument, or respectively, the instrument shaft 10 at whose end the effecter 15, for example, a prism angled by 30° is disposed. The axis III intersects the axes I and II also in the invariant point 1, that is, at the intersection of the axes I and II. The axis IV is a secondary axis extending at a distance from, and parallel to, the axis III. It forms the longitudinal movement axis for the linear drive in the guide housing 17 for the axial movement of the instrument shaft 10 together with the effecter 15.

The support member 2a for the apparatus includes in the embodiment as shown in the figures, a motor which is adapted to rotate an angled support member 4 mounted below and on the support member 2a so as to be rotatable about the axis I by way of a self-locking screw drive 3. The angled support member 4 carries, displaced to the side of the axis I below the carrier 2, a segment 5 of a worm gear which has a center point 6 of rotation on the axis I, the axis II intersecting the axis I in the center point 6. A housing 7 is slidably supported on the segment 5 by means of a guide structure 8 such that the housing 7 is movable parallel to the segment curvature or rather along the segment. The housing 7 includes a worm gear 9 which is operated by a gear motor 12 via a universal joint 11. The worm gear 9 is in engagement with the gear segment 5 and, upon rotating, tilts the gear segment 5 together with the housing 7 (see FIG. 3).

The housing 7 is supported by the angled support member 4 on the side with a certain distance from the plane defined by the axes I and III. The angled support member 4 in connection with the housing 7 mounted on the side thereof provide therefore an arrangement wherein the axis IV which extends through the center of the housing 7 and forms the angled center axis of the linear drive extends sidewardly displaced with respect to the instrument shaft or trocar axis III. With this sideward displacement of the axes III and IV the trocar 30 or the instrument shaft 10 can be removed easily through the linear drive without any interference.

Figure 1:
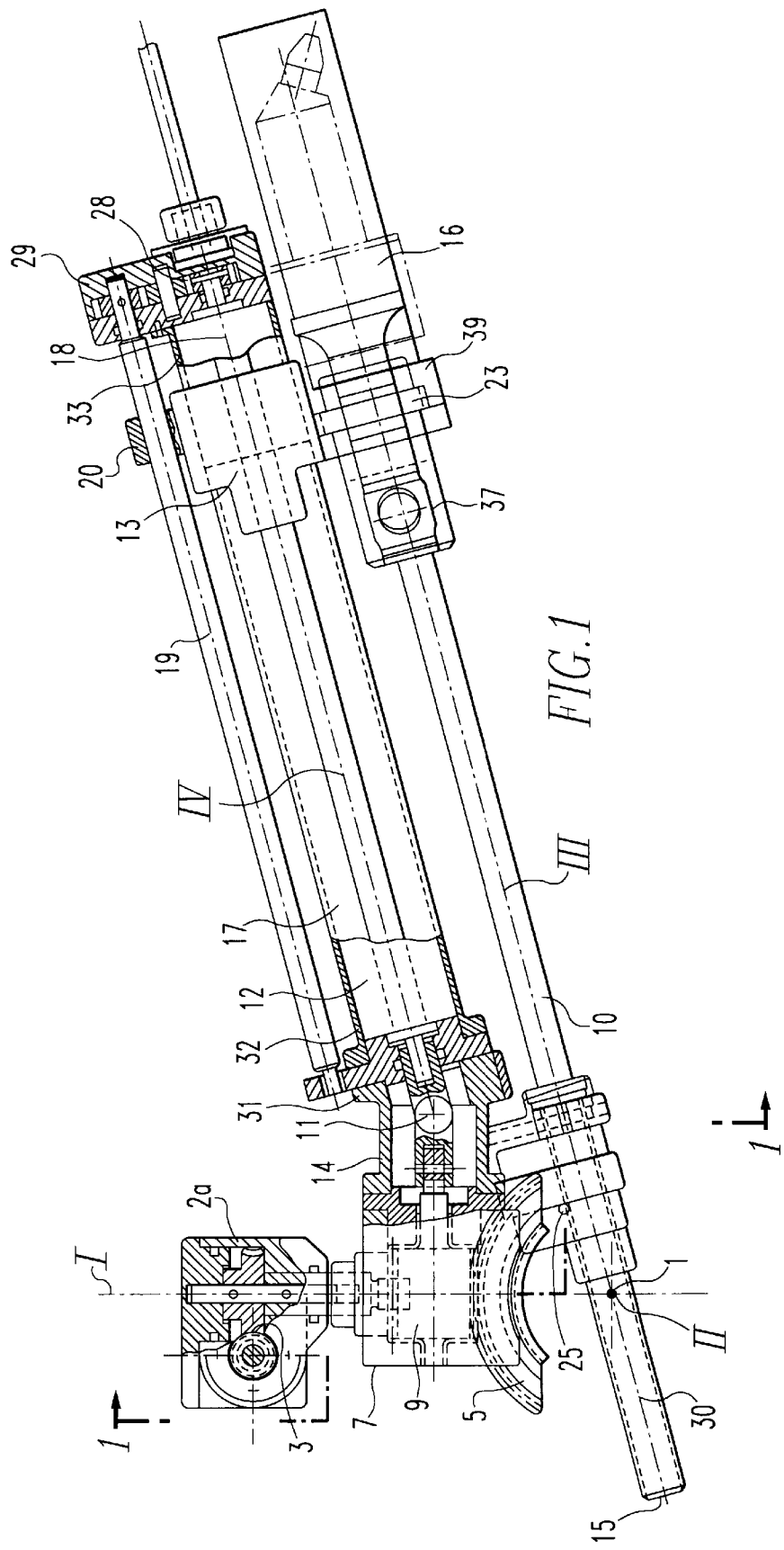
FIG. 1 is a side view of the apparatus according to the invention.
Figure 2:
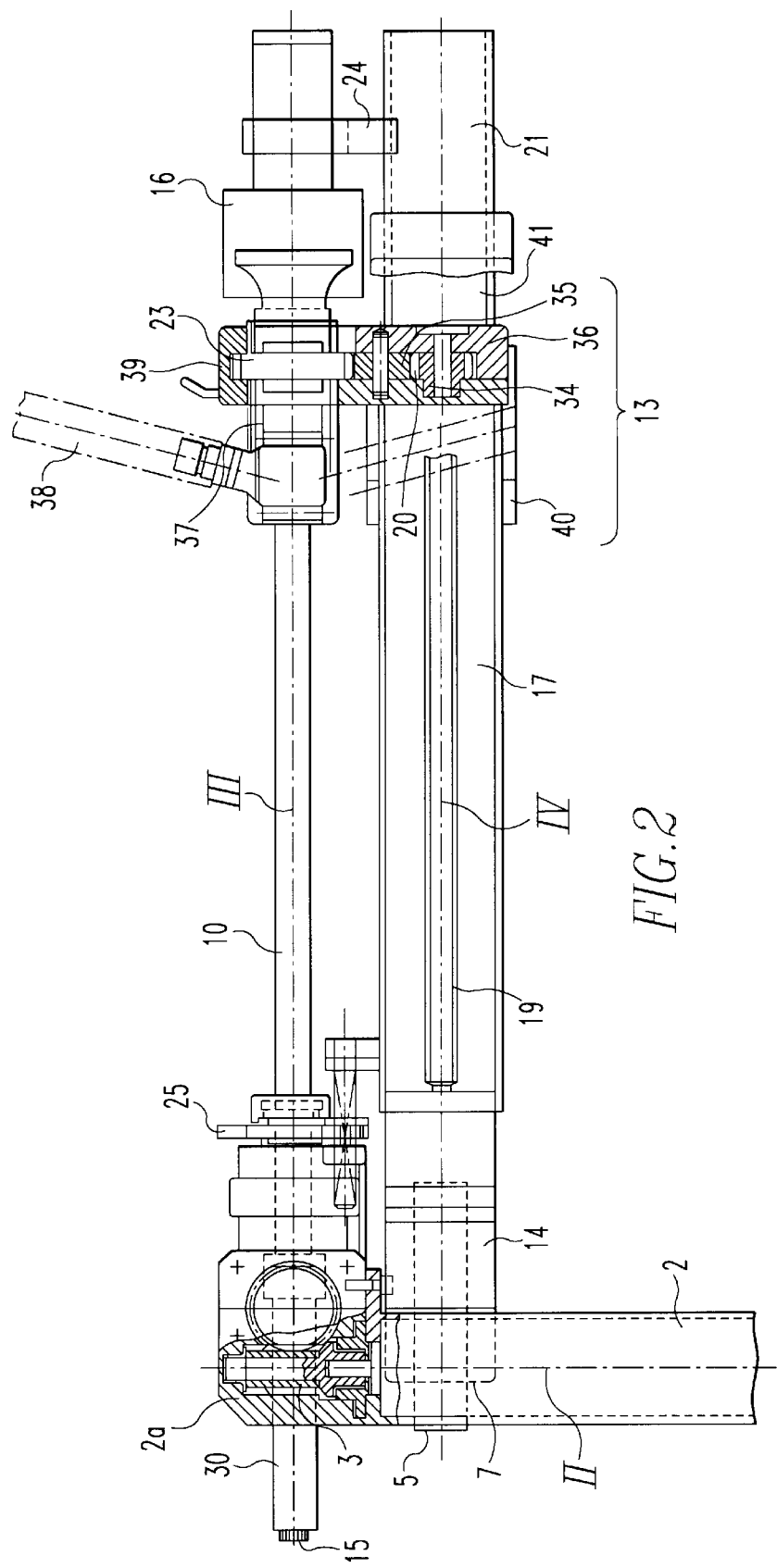
FIG. 2 is a top view of the apparatus shown in FIG. 1.

At its side, the housing 7 carries an angled double flange structure 14 on which the guide and linear drive elements with their center axis IV and the instrument shaft 10 with its instrument axis III are mounted. The effecter 15 is disposed at the front end of the shaft 10. At its rear end, there is a camera 16 (see FIG. 1), the axes II and IV being spaced from one another. It is important, however, that the effecter 15 with the instrument shaft 10 is rotatable with respect to the camera 16 and the camera 16 is, with regard to the guide housing 17, axially movably supported by means of a guide member 13, but is not rotatable relative thereto. All these parts are, together with the axis IV, slightly angled upwardly with respect to the housing 7. As a result, all components tilt about the axis II together with the housing 7 and about the invariant point, with respect to the angled support member 4 and, with the angled support member 4 about the axis I.

The guide housing 17 is the major guide element for the shaft 10. The guide member 13 is slidably supported on the guide housing 17 which is supported on the angled part 31 of the double flange 14. The guide housing 17 has a front end 32 in which the gear motor 12 effecting the pivot movement about the axis II is supported and a rear end 33 in which the motor 15 effecting the linear movement of the guide member 13 is supported. The linear movement of the guide member 13 on the guide housing 17 is generated by a threaded spindle 19 which is rotatably supported in the guide housing 17 and extends parallel to the guide housing 17 and which is driven by the motor 18. The threaded spindle 19 extends through a spindle nut 20 of the guide member 13 and is rotatably supported at the front end 32 and at the end portion 29 of the guide housing 17 so that, upon rotation of the spindle 19, the guide member 13 is moved linearly along the guide housing 17. The spindle 19 is driven by the gear transmission 28 which is also supported in the end portion 29 and which is connected to the motor 18 so as to be driven thereby.

The guide member 13 consists of the followings parts: A front part 40 which is slidably supported on the guide housing 17, a plate 31 which is mounted on the side of front part 40 onto which another support plate 36 is screwed and which supports within a gear 23 and the intermediate gear 35 which is in meshing engagement with the gear 23. On the other side, the support plate 36 carries a transmission 41 with a motor 21 for driving the gears 23 and 35. The camera 16 is mounted onto the motor 21 by means of a camera support bracket 24 whereby the camera 16 or rather its picture receiving CCD chip is disposed on the axis II behind the instrument shaft 10 or its adapter 37 in such a way that the image plane of the optical system in the instrument shaft 10 is disposed on the CCD chip. Also mounted on the instrument shaft 10 is the glass fiber cable 38 for the illumination of the operation area. Since the shaft with the effecter and the connection for the cable 38 are rotatable by the adapter 37, but the chip or the camera is not rotatably supported the orientation of the camera picture remains unchanged when the instrument shaft 10 is rotated by the motor 21. The cable connection serves as outer position indicator. The adapter 37 is disposed rotatably in an outer support structure 39, which is mounted to the plate 34 supporting the upper end of the instrument shaft 10, and is rotated by the gear 23 which is mounted on the shaft 10 so as to be in meshing engagement with the intermediate gear 35.

As already mentioned, the camera 16 and the instrument shaft 10 with the effecter 15 are supported on the guide member 13 or the motor 21 mounted thereto such that these structures are rotatable about the axis III. The lower end part of the instrument shaft 10 with the trocar 30 are guided in a manner which will be described below. The rotation is generated by the motor 21, which is mounted along the axis IV on the guide member 13 which extends in spaced relationship parallel to the axis III through the invariant point (see FIG. 20). The transmission output shaft which is supported on the support 36 carries a gear 22 which, by way of the intermediate gear 35, drives the gear 23 which is disposed adjacent the plate 34 of the guide member 13 on the adapter 37 of the instrument shaft 10 and which is supported by the support structure 39. The instrument shaft 10 and the effecter 15 can therefore be rotated by the motor 21 by way of the gear 23.

The instrument shaft 10 with the effecter 15 and the camera 16 which is fixed by the camera support bracket 24 so as not to be rotatable can therefore be moved together with the guide member 13 and the elements associated therewith in a linear fashion along the axis III while the instrument shaft 10 with effecter 15 remains rotatable. The effecter end of the shaft 10 which is movably supported in the trocar 30 which itself is guided in an opening 27 of a trocar receptor 25 is mounted on the angled support member 4 and includes an engagement lever 26 for closing the opening 27. The trocar is held in the opening 27 by the engagement lever 26 during longitudinal movement of the trocar, but it can be removed from the opening 27 when the lever 26 is pivoted to an open position (see FIG. 3). The shaft 10 with the upper parts described earlier and with the lens system mounted thereon can consequently be pulled out of the mounted trocar and out of the support structure 39 in which it is held so that it can be easily replaced by a fast release lock which however is not shown. The mounting structures are of such versatile design that they can accept different types of instruments and trocars. However, the camera 16 remains in place. If necessary, it can be removed or replaced separately.

The whole unit can be rotated about the axis I whereby the shaft 10 is rotated about the axis I in the invariant point 1. The cone angle described by the shaft 10 can be moved by pivoting about the axis II and the distance of the effecter 15 from the treatment location can be adjusted by linear movement of the shaft 10 along the axis III.

The instruments needed for an operation are inserted into the abdominal cavity of a patient through the trocar 30 after being placed into the adapter 37 of the instrument shaft. In this procedure, the trocar remains in a certain position while the instrument shaft 10 is inserted along the axis III through the trocar 30 into the abdominal cavity. For this reason, the trocar receptor 25 is mounted on the part of the linear guide structure which is mounted on the housing 7 and is not linearly movable whereas the instrument receiver is supported in the guide member 13 or its support structure 39. The various operating positions of the instruments can be accommodated by pivot adjustment about the axis I, II, and III. If the axis I is arranged so as to extend normal to the floor through the invariant point 1, the instrument follows, when rotated about the axis I, a circle or cone area depending on the angular position of the axis II relative to the axes I. In this way, the end of the instrument, that is, the effecter 15 can be pivoted in the abdominal cavity to the right and to the left about the axis I and up and down about the axis II. The instrument end can be adjusted axially from the trocar insert point through the abdominal cavity. Since the camera 16 is disposed in this arrangement of the axes on the instrument shaft 10 on the axis III in such a way that it is not rotated with the instrument shaft 10, the picture generated by the CCD chips of the camera will maintain its proper vertical orientation even if adjustments are made about all three axes and the prism of the effecter 15 is rotated with the shaft 10. The monitor picture is not turned in the process.

For operation, the sterilized apparatus is assembled and placed onto support system which is pre-mounted on the operation table. The two axes I and II are adjusted to the invariant point and the support system is arrested in this position. Then the trocar 30 and the instrument shaft 10 are mounted onto the apparatus. Then the instrument instrument can be moved to the desired position in stepless fashion.

What is claimed is:

1. An apparatus for guiding surgical instruments for endoscopic surgery, comprising a carrier, a support member mounted on said carrier so as to be rotatable about a first axis, a circularly curved gear segment mounted on said support member below said carrier and having a second axis in the center of curvature of said gear segment and intersecting said first axis in an invariant point disposed at a distance from said carrier, a housing structure slidably supported on said gear segment so as to be pivotable about said second axis, a trocar support structure mounted on said housing structure and having an opening for receiving an instrument shaft having a third axis extending through said invariant point, a guide housing also mounted on said housing structure and extending therefrom in parallel alignment with said third axis, a guide member axially movably supported on said guide housing and rotatably supporting one end of said instrument shaft in a releasable fashion, and a camera firmly mounted on said guide member in alignment with said third axis at the end of said instrument shaft, said instrument shaft having at its front end, an optical system and said camera having an image plane receiving an image from said optical system, said optical system being rotatable with said instrument shaft relative to said camera which remains stationary relative to said guide member.

2. An apparatus according to claim 1, wherein said guide member includes a front part slidably supported on said guide housing, a holding plate mounted on said guide housing, a support plate screwed onto said holding plate and carrying at one side thereof a transmission gear and an intermediate gear in meshing engagement therewith, a motor mounted on the other side of said holding plate in driving engagement with said transmission gear, said camera being mounted onto said motor, a rotatable adapter supported on a sidewardly extending support structure mounted on said holding plate for supporting the other end of said instrument shaft, said adapter being rotatable by said transmission gear which is in engagement with said intermediate gear, said adapter receiving said instrument shaft for rotating said instrument shaft.

3. An apparatus according to claim 1, wherein the front end of said instrument shaft is movably supported in a trocar so as to be removable, said instrument shaft being received in an opening of a trocar receptor which is supported on said support member, said trocar receptor having an engagement lever for holding said instrument shaft in position when said engagement lever is in a locking position but releasing said instrument shaft for removal of said instrument shaft from said trocar receptor when said engagement lever is in a releasing position.

* * * * *